US00PP22772P2

(12) United States Plant Patent
Madsen

(10) Patent No.: US PP22,772 P2
(45) Date of Patent: Jun. 5, 2012

(54) ***CAMPANULA* PLANT NAMED 'PKMF03'**

(50) Latin Name: *Campanula formanekiana*
Varietal Denomination: PKMF03

(75) Inventor: Christian Hald Madsen, Korsor (DK)

(73) Assignee: Gartneriet PKM A/S, Odense N (DK)

( * ) Notice: Subject to any disclaimer, the term of this patent is extended or adjusted under 35 U.S.C. 154(b) by 0 days.

(21) Appl. No.: 12/929,017

(22) Filed: Dec. 22, 2010

(51) Int. Cl.
*A01H 5/00* (2006.01)

(52) U.S. Cl. ..... Plt./414

(58) Field of Classification Search ..... Plt./414
See application file for complete search history.

*Primary Examiner* — Annette Para
(74) *Attorney, Agent, or Firm* — Foley & Lardner LLP

(57) ABSTRACT

A new and distinct cultivar of *Campanula* plant named 'PKMF03', characterized by having compact plant habit; dense and bushy pyramidal plant form; vigorous growth habit; and large upright white flowers.

8 Drawing Sheets

Latin name of the genus and species of the plant claimed: *Campanula formanekiana.*

Variety denomination: 'PKMF03'.

BACKGROUND OF THE INVENTION

The present invention relates to a new and distinct cultivar of *Campanula* plant, botanically known as *Campanula formanekiana*, commonly known as Bellflower, and hereinafter referred to by the name 'PKMF03'.

The new *Campanula*, 'PKMF03', is a product of a planned breeding program conducted by the inventor, Christian Hald MADSEN, in Søhus, Denmark. The objective of the breeding program is to develop a new *Campanula* variety with upright and compact plant form and white flowers.

The new *Campanula* cultivar originated from a cross made in August 2006 by the inventor between a proprietary selection of *Campanula formanekiana* named 11.06.0308-1 as the female parent, and a proprietary selection of *Campanula formanekiana* named 11.06.0308-2 as the male parent. The Inventor selected the new *Campanula* cultivar on the basis of its high number of cuttings per stock plant, short vernalization period and short forcing time after the vernalization, and white flower, slightly violet-blue at lobe tips.

Asexual reproduction of the new *Campanula* 'PKMF03' by terminal cuttings since March 2008 in Søhus, Denmark, has shown that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKMF03'. These characteristics in combination distinguish 'PKMF03' as a new and distinct cultivar:

1. Upright, compact plant habit;
2. Dense plant form, mainly due to short, upright, stiff stems;
3. Vigorous pyramidal growth habit, and less need for chemical growth retardation;
4. Higher number of flowers per plant;

5. More cuttings on each stock plant;
6. Less need for cold treatment for flower induction;
7. Shorter-period for forcing the flowers after the cold treatment; and
8. White flowers.

Of the commercial cultivars known to the inventor, the most similar in comparison to 'PKMF03' is 'PKMFOR168' (U.S. Plant Pat. No. 19,812). In side-by-side comparisons between the new *Campanula* 'PKMF03' and 'PKMFOR168' (U.S. Plant Pat. No. 19,812). conducted by the Inventor in Stige, Denmark, plants of the cultivar PKMF03 and 'PKMFOR168' differ in the following characteristics:

1. Plants of the new *Campanula* have white flowers whereas plants of PKMFOR168 have violet-blue flowers.
2. Plants of the new *Campanula* have smaller flowers than plants of PKMFOR168.
3. Plants of the new *Campanula* have smaller buds than plants of PKMFOR168.

BRIEF DESCRIPTION OF THE PHOTOGRAPHS

The accompanying colored photographs illustrate the overall appearance of the new cultivar 'PKMF03', showing the colors as true as it is reasonably possible to obtain in colored reproductions of this type. Colors in the photographs may differ slightly from the color values cited in the detailed botanical description, which more accurately describe the actual colors of 'PKMF03'.

DETAILED BOTANICAL DESCRIPTION

Figure 1:
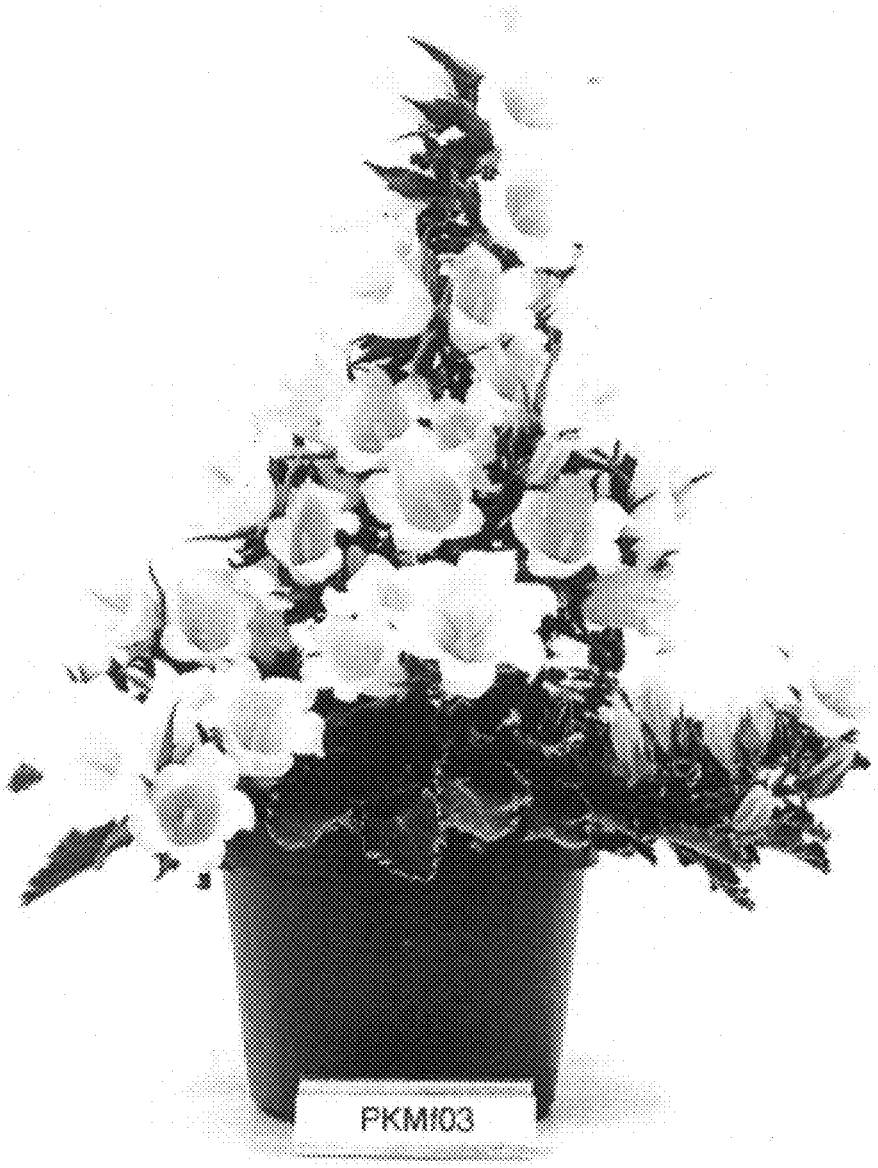
FIG. 1 shows a side perspective view of a typical flowering plant of 'PKMF03'.
Figure 2:
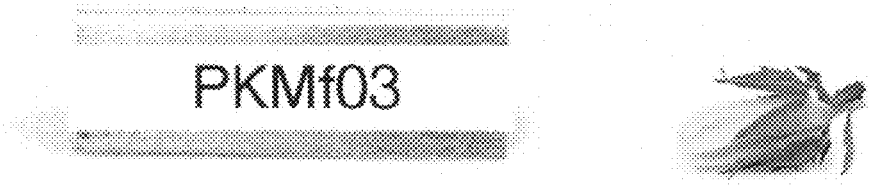
FIG. 2 shows a side perspective view of typical bud of 'PKMF03'.
Figure 3:
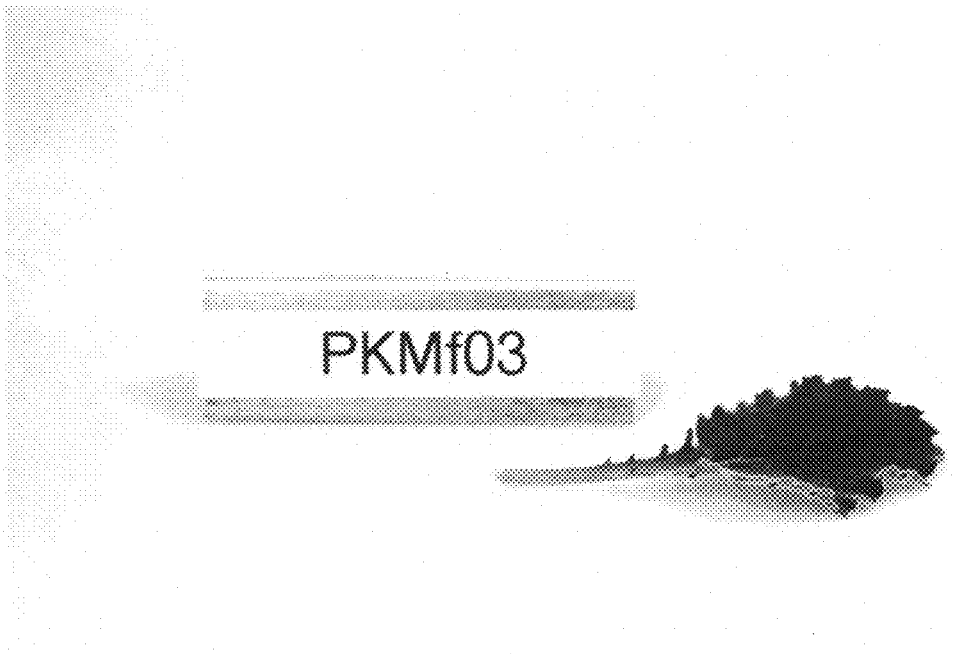
FIG. 3 shows a close-up view of a typical 'PKMF03' leaf.
Figure 4:
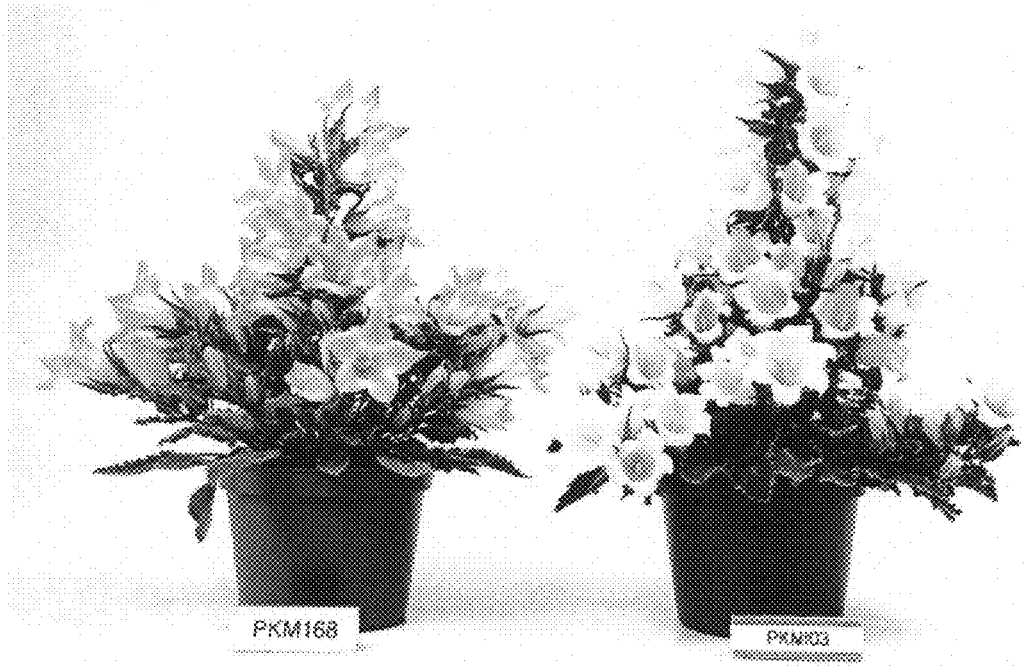
FIG. 4 shows a comparison view of a typical flowering plant of 'PKMF03' with a typical flowering plant of 'PKMFOR168'.
Figure 5:
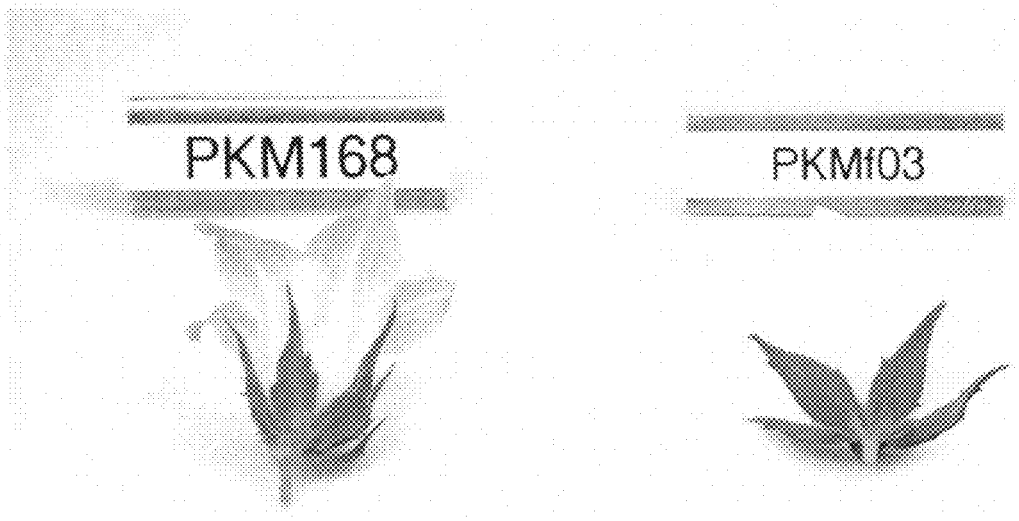
FIG. 5 shows a comparison view of a close-up view of a typical 'PKMF03' sepal shape with a close-up view of a typical 'PKMFOR168' sepal shape.
Figure 6:
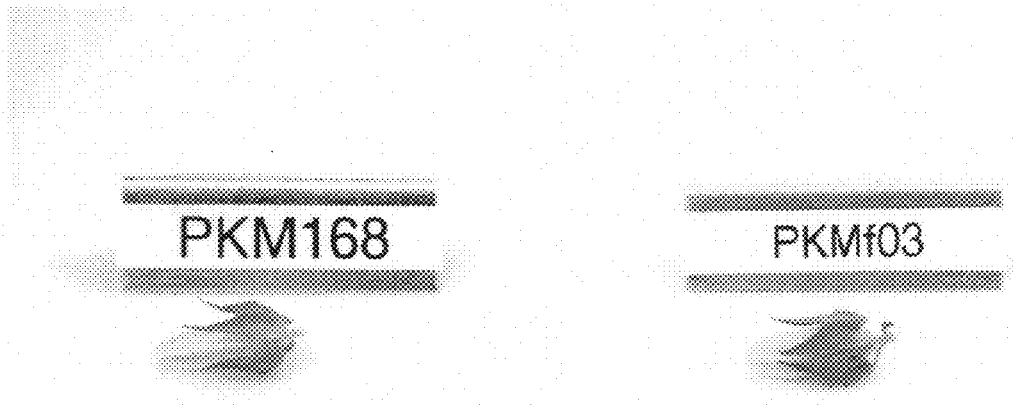
FIG. 6 shows a comparison view of a typical 'PKMF03' bud with a typical 'PKMFOR168' bud.
Figure 7:
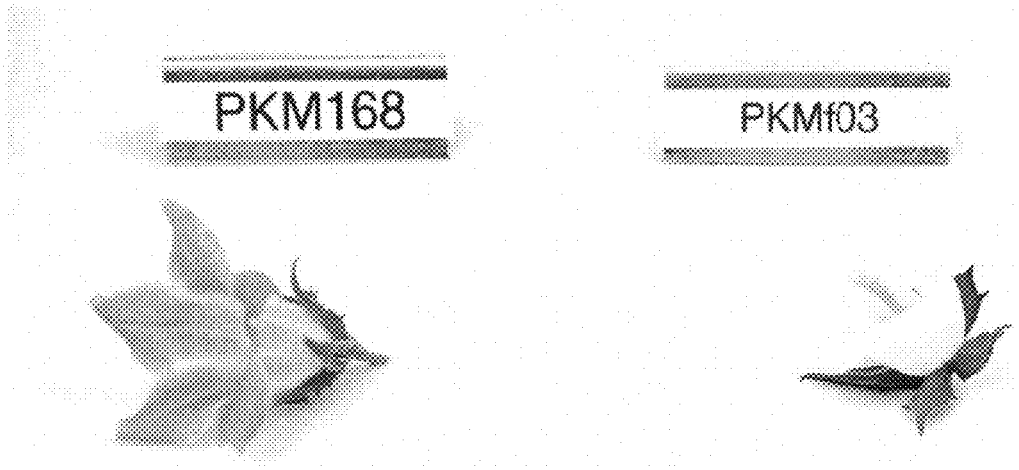
FIG. 7 shows a comparison view of a typical flower of 'PKMF03' with a typical flower of 'PKMFOR168'.
Figure 8:
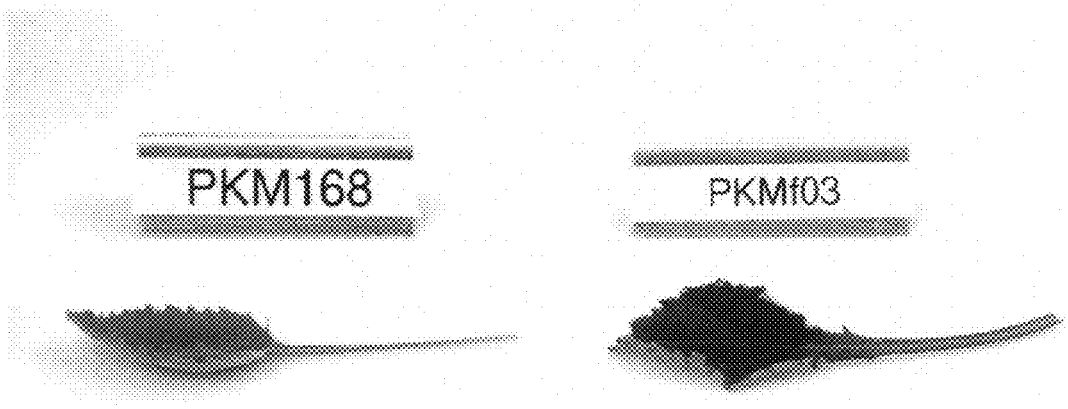
FIG. 8 shows a comparison view of a close-up view of a typical leaf of 'PKMF03' with a typical leaf of 'PKMFOR168'.

The new *Campanula* 'PKMF03' has not been observed under all possible environmental conditions. The phenotype of the new cultivar may vary significantly with variations in environment such as temperature, light intensity, day length, and fertility level without any variance in genotype.

The aforementioned photographs, together with the following observations, measurements and values describe plants of the new *Campanula* 'PKMF03' as grown in a heated and lighted, glass-covered greenhouse in Søhus, Denmark, under conditions which closely approximate those generally used in commercial practice. Plants of 'PKMF03' are grown in a glass-covered greenhouse where day temperatures in the greenhouse range from 18-22° C. and the average night temperatures is 16° C. Light levels used while growing plants of 'PKMF03' are 90 $Wm^2$ in long day photoperiodic treatments. No growth retardants were used when growing plants of the new *Campanula* 'PKMF03'.

The age of the 'PKMF03' plants described is 21 weeks old (short day growth for 10 weeks; 3 weeks at 5° C.; long day growth for 8 weeks) after cutting, as grown in 10.5 cm pots. The photographs and descriptions were taken during the spring/summer season when day temperatures in the glass-covered greenhouse ranged from 18-22° C. and when the night average temperature in the glass-covered greenhouse was 16° C.

Color references are made to The Royal Horticultural Society Colour Chart (R.H.S.), $5^{th}$ edition, except where general colors of ordinary significance are used.

Classification:

*Botanical.—Campanula formanekiana.*

Parentage:

*Female.—Campanula formanekiana* '11.06.0308-1'.

*Male.—Campanula formanekiana* '11.06.0308-2'.

Propagation:

*Type.*—Terminal vegetative cuttings.

*Time to initiate roots.*—About 12 to 15 days at 18 to 21° C. in tunnels in a greenhouse.

*Root description.*—Fine, well branched.

Plant:

*Form.*—Biennial, herbaceous plant with upright, compact plant habit. Produced as potted plant. Campanulate flowers in racemes. Freely branching with lateral branches forming at every node.

*Crop time.*—After rooting, about 14 weeks are required to produce finished flowering plants in 10.5 cm pots.

*Vigor.*—Vigorous.

*Size.*—Height (pot rim to top of plant plane): About 32-38 cm. Spread (width): About 25-30 cm in diameter.

*Stem.*—Shape: Round. Strength: Strong. Color: RHS 138B, green.

*Lateral branches.*—Quantity: About 25-35 per plant. Length (including flowers): About 25-35 cm. Diameter: About 2 mm to 3 mm. Basal branching: Present. Internode Length: About 20-30 mm.

Foliage:

*Quantity of leaves per lateral branch.*—8-9.

*Arrangement.*—Single.

*Length.*—Basal: About 2-6 cm; Apical: About 2-6 mm.

*Width.*—Basal: About 24-27 mm; Apical: 8-12 mm.

*Shape.*—Cordate to obovate, dentate.

*Apex.*—Cuspidate to rounded.

*Base.*—Cordate to truncate.

*Margin.*—Serate to Biserate.

*Texture.*—Pubescent on both sides.

*Color.*—Upper surfaces (young and mature foliage) RHS 137A; Under surfaces (young and mature foliage): RHS 138C.

*Venation.*—Pattern: Reticulate. Color: (Upper and under surfaces) RHS 138D, green.

*Petiole.*—Length: Basal: About 9 cm to 10 cm; Apical: 0-2 cm. Diameter: 1-3 mm. Texture: Pubescent. Color: RHS 138B, green.

Inflorescence:

*Flower arrangement and shape.*—Single, large campanulate flowers in racemes turning upright to outward; basipetal flowering habit.

*Natural flowering season.*—June-July.

*Flower longevity on the plant.*—Longevity of individual flowers is highly dependent on temperature and light conditions. Flowers persistent.

*Fragrance.*—Weak.

*Inflorescence size.*—Length: About 15-35 cm. Diameter: About 5-25 cm.

*Number of flowers per inflorescence.*—5-25.

*Quantity of flower buds and flowers per plant.*—150-250.

*Quantity of flower buds per lateral stem.*—5-10.

*Quantity of flowers per lateral stem.*—5-10.

*Flowers.*—Height: About 35-40 mm. Diameter: About 25-40 mm. Shape: Sympetalous, with acute petal lobes (about 15 mm long and 12-15 mm wide). Aspect: Upright to outward. Corolla color: RHS NN155D.

*Buds.*—Length: Up to 25 mm. Diameter: Up to 12 mm. Shape: Oblong, petals forming a ribbed tube. Color: RHS 157A, green-white.

*Petals.*—Arrangement: Single, sympetalous, campanulate. Quantity per flower: 5. Overall shape: Sympetalous with acute lobes. Apex: Acute. Base: Fused. Length: About 15 mm. Width: About 12-15 mm. Margin: Entire. Texture: Silky. Color (when opening): Upper surface: RHS NN155D, white; Under surface RHS NN155D, white. Color (when fully opened): Upper surface: RHS NN155D, white (at base) RHS 92D, violet-blue (at lobe tips). Under surface RHS NN155D, white. Fading: None observed. Sepals: Arrangement: Basally fused. Quantity per flower: 5. Overall shape: Broad Lanceolate.

*Apex.*—Acuminate.

*Base*: Sagittate.

*Length.*—About 30-40 mm.

*Width.*—About 10-20 mm.

*Margin.*—Serate to biserate.

*Texture.*—Pubescent.

*Color*: (*immature—both surfaces*).—RHS 138A, green.

*Color*: (*mature—both surfaces*).—RHS 138A, green.

*Peduncle.*—Strength: Strong. Length: About 15-25 mm. Diameter: About 3-4 mm. Color: RHS 138B, green.

*Pedicels.*—Yes.

Reproductive organs:

*Androecium.—Stamen: Quantity per flower:* 5. Anther: Shape: Lanceolate, antisepalous, introse, basifixed and two celled, screwing when withering. Length: About 12 mm. Color: Just before flower opening: RHS 10C, yellow; When withering: RHS 11B, yellow. Pollen: Amount: Plenty. Color: RHS 10B, yellow. Pistil: Quantity per flower: 1. Length: 30-40 mm. Stigma: Shape: Tripartite. Color: RHS 149C, yellow-green. Style: Length: 20-25 mm. Color: RHS155A, white. Ovary: Color: RHS155A with yellow (RHS17C) nectary.

Seeds: No seeds observed.

Fruit: None observed.

Growth retardants: No growth retardants were used in the breeding program.

Weather tolerance: Plants of the new *Campanula* have in general good tolerance to drought, rain and wind, with low temperature resistance to 0° C.

Disease/pest resistance: 'PKMF03' is not resistant to any diseases or pests typical to *Campanula* cultivars.

What is claimed is:

1. A new and distinct cultivar of *Campanula* plant named 'PKMF03', as illustrated and described herein.

* * * * *